(12) United States Patent
Hommann (10) Patent No.: US 7,445,613 B2
(45) Date of Patent: Nov. 4, 2008

(54) PRODUCT DELIVERY DEVICE WITH RAPID PISTON ROD SETTING

(75) Inventor: Edgar Hommann, Grossaffoltern (CH)

(73) Assignee: TecPharma Licensing AG, Burgdorf (CH)

( * ) Notice: Subject to any disclaimer, the term of this patent is extended or adjusted under 35 U.S.C. 154(b) by 618 days.

(21) Appl. No.: 11/023,285

(22) Filed: Dec. 27, 2004

(65) Prior Publication Data

US 2005/0137534 A1 Jun. 23, 2005

Related U.S. Application Data

(63) Continuation of application No. PCT/CH03/00419, filed on Jun. 25, 2003.

(51) Int. Cl.
*A61M 5/00* (2006.01)
*A61M 5/315* (2006.01)

(52) U.S. Cl. .................. 604/211; 604/187; 604/218; 604/224

(58) Field of Classification Search ............ 604/187, 604/211, 218, 224
See application file for complete search history.

(56) References Cited

U.S. PATENT DOCUMENTS

| | | | | |
|---|---|---|---|---|
| 5,092,842 | A | * | 3/1992 | Bechtold et al. ............ 604/135 |
| 5,112,317 | A | * | 5/1992 | Michel ...................... 604/208 |
| 5,279,586 | A | * | 1/1994 | Balkwill .................... 604/207 |
| 5,308,340 | A | * | 5/1994 | Harris ....................... 604/208 |
| 5,514,097 | A | | 5/1996 | Knauer |
| 5,591,136 | A | | 1/1997 | Gabriel |
| 6,277,097 | B1 | | 8/2001 | Mikkelsen et al. |
| 6,932,794 | B2 | * | 8/2005 | Giambattista et al. ....... 604/207 |

FOREIGN PATENT DOCUMENTS

| | | |
|---|---|---|
| DE | 35 33 735 C2 | 4/1987 |
| DE | 199 09 602 A1 | 9/2000 |
| EP | 0 295 075 B1 | 12/1991 |
| EP | 0 327 910 B1 | 4/1992 |
| EP | 0 450 905 B1 | 10/1995 |
| EP | 0 956 874 B1 | 11/1999 |
| WO | WO 88/08724 | 11/1988 |
| WO | WO 91/10460 | 7/1991 |
| WO | WO 96/07443 | 3/1996 |
| WO | WO 99/03522 A1 | 1/1999 |
| WO | WO 01/72361 A1 | 10/2001 |
| WO | WO 02/30495 A2 | 4/2002 |

* cited by examiner

*Primary Examiner*—Nicholas D. Lucchesi
*Assistant Examiner*—Victoria P Campbell
(74) *Attorney, Agent, or Firm*—Dorsey & Whitney LLP; David E. Bruhn (57) ABSTRACT

A substance delivery device including a casing formed by a first casing portion for a substance reservoir including a piston, a piston rod movable in an advancing direction to move the piston toward an outlet of the reservoir to deliver the substance, a dosing element which performs a dosing movement relative to the casing and, together with the piston rod, performs a delivery movement in the advancing direction, a dosing member connected to the dosing element wherein the dosing member is movable generally transversely to the piston rod to enable the piston rod to be moved counter to the advancing direction, a resetting element movably connected to the first casing portion to perform dosing member and piston rod disengaging and engaging movements, and a cam gear coupling the resetting element to the dosing member, wherein the cam gear forms a guiding rail on which the dosing member is guided.

13 Claims, 6 Drawing Sheets

PRODUCT DELIVERY DEVICE WITH RAPID PISTON ROD SETTING

PRIORITY CLAIM

This application is a continuation of International Patent Application No. PCT/CH02003/000419, filed on Jun. 25, 2003, which claims priority to German Application No. DE 102 29 138, filed on Jun. 28, 2002, the contents of which are incorporated in their entirety by reference herein.

BACKGROUND

The present invention relates to devices and methods for delivering a substance or product, including medicinal products, in selected doses or amounts. The product can be administered directly during delivery, for example by injection. The device and method can also, however, be used in conjunction with an administering means, for example a pressure injector or injection means, or an atomising means such as that associated with an inhaler. When delivering product in the latter applications, the desired product dosage is set and delivered into the subsequent, actual administering means.

Known injection apparatus, one of which is, for example, described in WO 99/03522, typically comprise a piston in a reservoir filled with product, wherein the piston is moved in order to deliver the product from the reservoir. The delivery movement of the piston is performed by means of a piston rod. For selecting the product dosage to be delivered and for delivery itself, the known apparatus further comprise a dosing and activating means which is coupled to the piston rod. The known dosing and activating means comprise a dosing member which is in direct engagement with the piston rod. By selecting the dosage, the piston rod is axially advanced a selected distance, relative to the dosing member, towards the piston. The dosing and activating means is then advanced with the dosing member and the piston rod. During this delivery movement, the piston rod presses against the piston, which therefore advances in the reservoir towards a reservoir outlet, thus delivering the selected product dosage. The procedure of selecting the dosage and delivering the product can be repeated until the length of the piston rod available for selecting the dosage is used. In the device of WO 99/03522, the piston rod is a threaded rod and the dosing member a threaded nut which are in threaded engagement with each other. If the piston rod is to be used again for subsequent administering of product, after the reservoir has been filled or exchanged, then it has to be rotated back, relative to the dosing member, along its threaded length used for selecting the dosage, which is awkward.

In another known design of product delivery devices, the piston rod is formed as a toothed rod and the dosing member as an elastic catch which engages with the serrated teeth of the piston rod. In devices of this type, resetting the piston rod is generally not possible.

SUMMARY

It is an object of the present invention to provide a product delivery device and method wherein, once a dosage has been selected, the device can be rapidly and comfortably reset or returned to an initial state extant before the dosage was selected.

In one embodiment, the present invention comprises a substance delivery device comprising a casing formed by a first casing portion for a substance reservoir including a piston, a piston rod movable in an advancing direction to move the piston toward an outlet of the reservoir to deliver the substance, a dosing element which performs a dosing movement relative to the casing and, together with the piston rod, performs a delivery movement in the advancing direction, a dosing member connected to the dosing element and movable generally transversely to the piston rod to enable the piston rod to be moved counter to the advancing direction, a resetting element movably connected to the first casing portion to perform dosing member and piston rod disengaging and engaging movements, and a cam gear coupling the resetting element to the dosing member, wherein the cam gear forms a guiding rail on which the dosing member is guided.

In one embodiment, a product or substance delivery device in accordance with the present invention comprises a casing, a piston rod, a dosing and activating means and a dosing member in engagement with the piston rod. The casing comprises a casing portion which accommodates a reservoir filled with product. In some embodiments, the casing portion can directly form the reservoir. In some preferred embodiments, however, it forms a holder for a product container which can be inserted. The reservoir comprises an outlet and is sealed by a piston at an end facing away from the outlet, wherein the piston can be shifted in an advancing direction towards the outlet, in order to force the product through the outlet. In some embodiments, the piston can be a fixed component of the device. In some embodiments, however, the piston can be a component of the product container and can be exchanged together with the container, as is common in devices and methods for self-administering. Self-administering within the context of a therapy, for example, administering insulin or growth hormone, thus represents one preferred area of use for the present invention.

In one embodiment, the dosing and activating means is associated with or mounted by the casing, such that it can perform a delivery movement in the advancing direction and a dosing movement, relative to the casing. In some embodiments, the dosing member is in engagement with the dosing and activating means, preferably in a positive lock, such that it is exactly slaved in the delivery movement. It is also in engagement with the piston rod. The engagement between the dosing and activating means and the dosing member and the engagement between the dosing member and the piston rod are such that the dosing member is moved in a dosing movement relative to the casing and relative to the piston rod by the dosing movement of the dosing and activating means. The dosing and activating means and the piston rod can thus be connected to each other such that they can shift axially relative to each other but are secured against rotating, for example with respect to a longitudinal axis of the piston rod, while the dosing member is axially and linearly guided in the casing and is in threaded engagement with the piston rod. In this case, the dosing movement of the dosing member can be a translational movement counter to the advancing direction.

In some preferred embodiments, the dosing and activating means and the dosing member are connected to each other such that they are secured against rotating and secured against shifting with respect to the axial direction. The dosing and activating means and the dosing member thus jointly perform not only the delivery movement, but also the dosing movement. As also in the alternative example, the engagement between the dosing member and the piston rod permits the dosing movement of the dosing member relative to the piston rod and slaves the piston rod during the delivery movement.

Although the engagement between the dosing member and the piston rod can be a frictional lock, as is, for example, described in DE 199 45 397, a positive-lock engagement with respect to the delivery movement and the dosing movement may be preferred. In some preferred embodiments, the dosing member is a threaded member which is in threaded engagement with the piston rod. Although a threaded engagement may be preferred, the piston rod can instead also be formed as a toothed rod and the dosing member as an elastic catch, such as are known in principle.

The dosing member can be moved transversely with respect to the piston rod, in order to be able to release the engagement which exists for selecting the dosage and for delivery. When the engagement is released, the piston rod can be moved back, i.e. reset or returned, counter to the advancing direction, as far as a rearmost initial position. In the rearmost initial position, the entire length of the piston rod effective for dosing is again available.

If the dosing member is a threaded member and the piston rod is correspondingly a threaded rod, then in the threaded engagement, the dosing member encompasses the piston rod over a circumference, measured as an arc, of at most 180°, in order to enable it to move transversely relative to the piston rod. In a preferred embodiment as a threaded member, the dosing member is formed as an axially split threaded nut, preferably as a split threaded member consisting of two nut halves arranged such that they can be moved transversely with respect to the piston rod, in opposite directions, out of engagement.

If the piston rod is a toothed rod and the dosing member is a catch which can be elastically bent away from the piston rod or a catch means comprising a number of such catches, the transverse movement of the dosing member for releasing the engagement with the piston rod is not understood as the elastic bending away for the purpose of dosing, common in such dosing members, but rather a transverse movement in which the catch or catches are moved as far as a disengaging position in which it does not protrude into the tooth gaps of the toothed rod portion of the piston rod due to its elasticity force, but is rather free from the piston rod.

The device and method in accordance with the present invention also comprises a resetting and activating element which is connected to the casing in such a way that it can perform a disengaging and engaging movement relative to the casing. In a preferred embodiment, the resetting and activating element comprises or forms a second casing portion. In principle, however, it can also be an additional element which is movably attached to the casing.

In some embodiments, the resetting and activating element and the dosing member are coupled to each other by a cam gear. The cam gear converts the disengaging movement of the resetting and activating element into the transverse movement of the dosing member which guides the dosing member out of its engagement with the piston rod. In the other direction, the cam gear also converts the engaging movement of the resetting and activating element into the transverse movement of the dosing member which guides the dosing member back into engagement with the piston rod. The transverse movement of the dosing member is a movement guided by a positive lock, along a guiding rail which points or extends transversely with respect to the longitudinal axis and may be referred to as the transverse guiding rail. In some embodiments, the dosing member is preferably guided directly on the transverse guiding rail. In this embodiment, the dosing member can form a sliding piece. The transverse guiding rail encloses the dosing member, or, as applicable, a transfer piece connected to the dosing member and guided on the transverse guiding rail, on both sides, such that the dosing member is prevented from moving in or counter to the advancing direction during its transverse movement in and out of engagement with the piston rod by being guided on the transverse guiding rail.

By means of the cam gear, which is coupled to the resetting and activating element and to the dosing member, the piston rod can be reset when the casing is closed. The resetting and activating element is activated relative to the casing such that it performs its disengaging movement. The disengaging movement is automatically transferred by the cam gear into the transverse movement of the dosing member which releases the engagement with the piston rod. As applicable, the device is also moved to a position in which, when the engagement is released, the piston rod falls or preferably slides counter to the advancing direction into an initial position due to the effect of gravity.

In some preferred embodiments, as already mentioned, the resetting and activating element is formed by a second casing portion. The first and second casing portion can be sleeve parts which are screwed together. These are preferably the two casing portions which have to be screwed apart in order to exchange or refill the reservoir. In some embodiments, the movement of the two casing portions relative to each other, performed when they are screwed apart, can simultaneously also be the disengaging movement. The two casing portions can in principle also be connected to each other by means of a plugging connection and/or locking connection which does not require the casing portions to rotate relative to each other. Connecting the casing portions by means of threaded engagement, however, is one preferred embodiment, since this enables the disengaging movement and engaging movement to be performed in a finely controlled way.

In principle, the resetting and activating element need not form a casing portion itself. It can also be an additional part which is connected, in some preferred embodiments, by means of threaded engagement, to the casing, for example to the first casing portion or a second casing portion.

In some embodiments, the cam gear preferably forms at least one other guiding rail for coupling the resetting and activating element to the dosing member. A gear input member connected to the resetting and activating element and a gear output member connected to the dosing member form a cam member and an engagement member of the cam gear. The cam gear is provided with a guiding rail on which the engagement member is guided in a guiding engagement. This guiding engagement transfers the disengaging movement and engaging movement of the resetting and activating element into the associated transverse movement of the dosing member relative to the piston rod. In some embodiments, the guiding rail can be a curved arc running or extending around the piston rod, on which the engagement member is raised from the piston rod in the event of rotation between the cam member and the engagement member about the piston rod. In some preferred embodiments, the guiding rail runs in the longitudinal direction of the piston rod and exhibits an inclination with respect to the piston rod, i.e., with respect to the longitudinal direction of the piston rod. Although the guiding rail can also be curved in this embodiment, the inclination may exhibit a constant angle of inclination. In some preferred embodiments, the guiding rail is continuously inclined, i.e., has no kinks and no cracks.

In one preferred embodiment, the dosing member and the gear output member are separate bodies which can be moved relative to each other in the longitudinal direction of the piston rod. In principle, however, it would also be conceivable to form the dosing member and the gear output member in one part. In the preferred embodiment in two parts, the gear output member grips behind the dosing member, transversely with respect to a normal onto a longitudinal axis of the piston rod, in order to draw the dosing member out of engagement with the piston rod.

In another equally preferred embodiment, the resetting and activating element and the gear input member are separate bodies. In principle, however, it is also the case here that the resetting and activating element and the gear input member can be embodied in one part. In the preferred embodiment in two parts, the resetting and activating element and the gear input member are preferably connected to each other such that they can be moved relative to each other along the longitudinal axis of the piston rod and/or rotated relative to each other about the longitudinal axis of the piston rod. The ability of the gear input member to move relative to the resetting and activating element is particularly advantageous when the resetting and activating element forms a portion of the casing.

In some preferred embodiments, a spring element is provided and arranged such that it is tensed by the engaging movement of the resetting and activating element and, during the disengaging movement, moves the gear input member relative to the gear output member, due to its tension force. This spring element can be formed by an equalization spring such as is commonly used to press a container filled with the product in the advancing direction until it abuts the casing. Such an equalization spring serves generally to equalize tolerances in length between a product container accommodated by the casing and other components of the device. The gear input member and the gear output member can advantageously be moved relative to each other using such an equalization spring. This is easily possible when the relative movement is parallel to the longitudinal axis of the piston rod or comprises an axial movement component.

BRIEF DESCRIPTION OF THE DRAWINGS

FIG. 10, including FIG. 10a-d, depicts the dosage indicator sleeve, in multiple representations.

DETAILED DESCRIPTION

Figure 1:
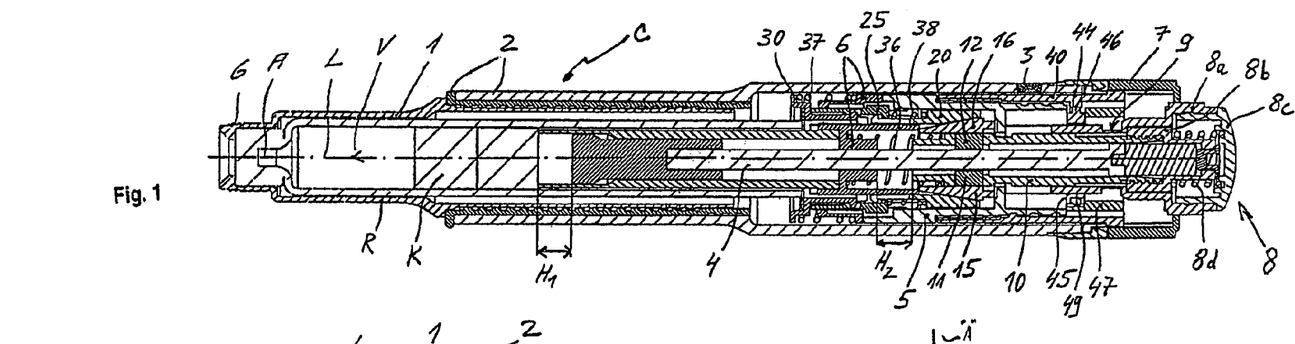
FIG. 1 depicts one embodiments of a product delivery device in accordance with the present invention in an initial state, before a dosage is selected for the first time.
Figure 2:
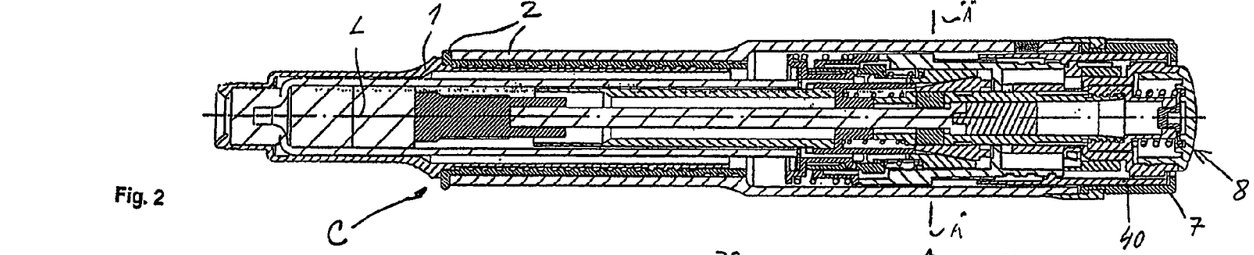
FIG. 2 depicts the product delivery device of FIG. 1 in an end state, in which a piston rod of the device assumes a foremost position and is in engagement with a dosing member.
Figure 3:
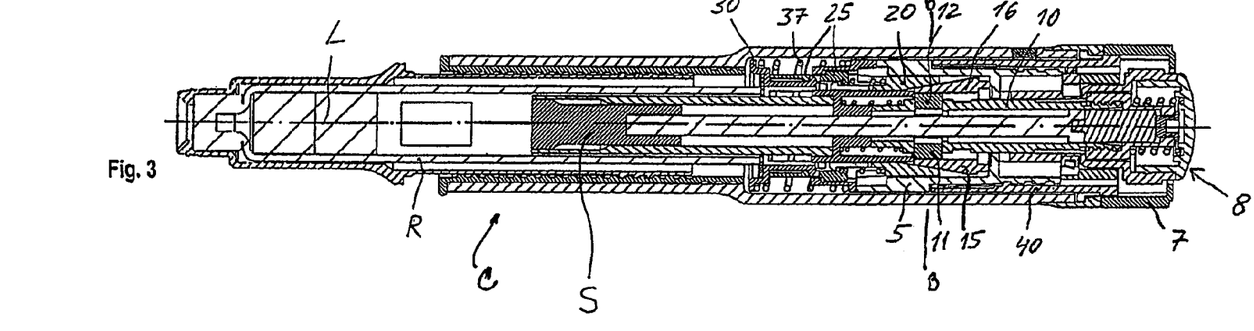
FIG. 3 depicts the product delivery device of FIG. 1 in a state in which the piston rod and the dosing member are out of engagement and the piston rod has been reset or returned to a rearmost initial position or state.

FIGS. 1-3 depict an embodiment of a device in accordance with the present invention for delivering a selected dosage or amount of a liquid product or substance. The product or substance can be a medicinal substance, for example insulin.

In one embodiment, a device in accordance with the present invention comprises a casing "C" in two parts, comprising a first, front casing portion 1 and a second, rear casing portion 2, which are each formed as sleeve parts. The two casing portions 1 and 2 are screwed together. The front casing portion 1 contains a reservoir "R" filled with the product. The reservoir R is formed by an exchangeable container, in this exemplary embodiment by a hollow-cylindrical ampoule. The container is inserted from the rear into the front casing portion 1 until it abuts a stopper formed by the front casing portion 1. At its front end, the container comprises an outlet "A" which is sterilely sealed by a septum. In order to be able to deliver the product from the reservoir R formed in this way, a cannula is introduced through the septum into the outlet A. At its rear end, the reservoir R is sealed tight by a piston "K". Product is displaced from the reservoir R, i.e. delivered through the outlet A, by advancing the piston K in an advancing direction "V", towards the outlet A, along a longitudinal axis "L".

The piston K is moved in the advancing direction V by means of a piston rod 4 which is linearly guided along the longitudinal axis L, i.e., axially, by the casing C. The piston rod 4 is coupled to a dosing and activating means comprising a dosing sleeve 7, a sleeve-shaped dosing and activating button 8 and a sleeve-shaped transfer element 10. A split dosing member is connected to said dosing and activating means. The dosing member is split axially, comprising two separate, substantially identical parts, a first dosing member component 11 and a second dosing member component 12. The first dosing member 11 and the second dosing member 12 are each in a threaded engagement about the longitudinal axis L, which is simultaneously also the longitudinal axis of the piston rod 4, with the piston rod 4 which is formed as a threaded rod. The first dosing member 11 and the second dosing member 12 are connected, secured against shifting axially and secured against rotating with respect to rotations about the longitudinal axis L, to the transfer element 10. However, both the first dosing member 11 and the second dosing member 12 can be moved relative to the transfer element 10 and, in particular, relative to the piston rod 4 in a transverse direction with respect to the longitudinal axis L. In order for them to be able to move in the transverse direction, the transfer element 10 linearly guides the first dosing member 11 and the second dosing member 12 by forming a guiding shaft pointing or extending transversely with respect to the longitudinal axis L for each of the two dosing members 11, 12, said guiding shaft simultaneously also acting as a block against axial shifting and a block against rotating. As can be more easily recognized on the basis of FIGS. 6 and 7, each of the guiding shafts comprises a side wall 10a pointing in the advancing direction V and a side wall 10b pointing counter to the advancing direction V. The side walls 10a and 10b each form a linear transverse guiding rail, pointing and/or extending transversely with respect to the longitudinal axis, for one of the dosing members 11 and 12. Each one of the dosing members 11 and 12 is enclosed and slide-guided between the two transverse guiding rails 10a and 10b of a guiding shaft, such that the two transverse guides formed by the pairs of transverse guiding rails 10a and 10b only permit sliding movements substantially exactly perpendicular to the longitudinal axis L. The dosing members 11 and 12 themselves form the guided engagement sliding pieces. The transverse guiding rails 10a and 10b, in conjunction with the dosing members 11 and 12, form a part of a cam gear.

Figure 8:
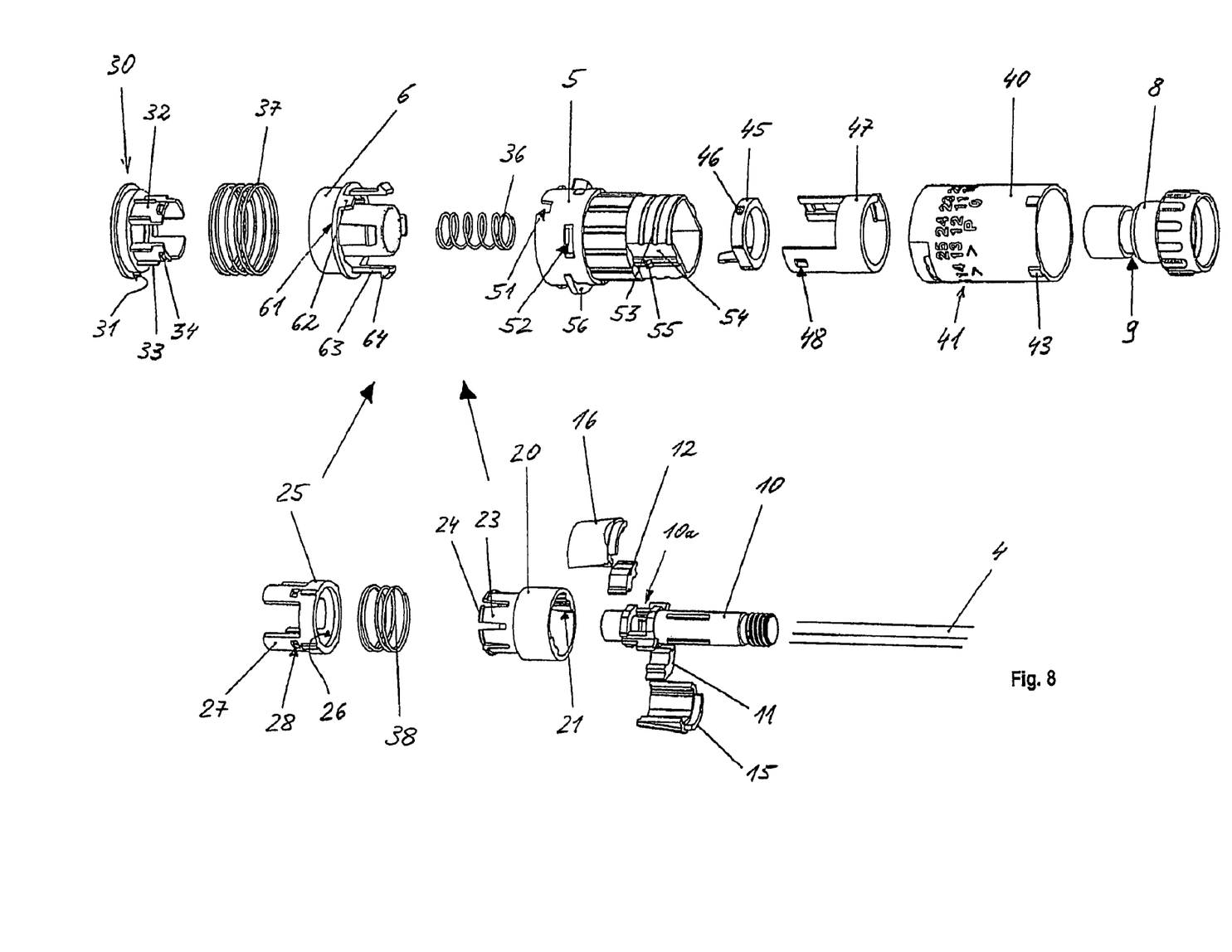
FIG. 8 depicts components of the device, in a three-dimensional representation.

With respect to the form, function and co-operation of the components which co-operate for dosing and delivering the product, reference can be made to FIG. 8.

The dosing and activating button 8 is detachably connected to the transfer element 10. The dosing and activating button 8 is composed of multiple individual parts, namely an outer sleeve part 8a protruding out of the rear casing portion 2, an inserted inner sleeve part 8b, an end button 8c which is inserted from the rear into the outer sleeve part 8a and locked, and a spring 8d which is axially tensed between the end button 8c and the inner sleeve part 8b. The inner sleeve part 8b serves to fasten the dosing and activating button 8 to the transfer element 10. The outer sleeve part 8a is accessible for the user for activating the administering apparatus. The outer sleeve part 8a is connected, secured against shifting, to the end button 8c and supported on the inner sleeve part 8b via the pressure-tensed spring 8d. The outer sleeve part 8a can be moved in and counter to the advancing direction V relative to the fastening part 8b and therefore also relative to the transfer element 10. The spring 8d presses the outer sleeve part 8a counter to the advancing direction V until it abuts the inner sleeve part 8b, such that it assumes the rear stopper position, shown in FIGS. 1 to 3, relative to the inner sleeve part 8b. Correspondingly, it can be moved relative to the inner sleeve part 8b and the transfer element 10 in the advancing direction V by pressing against the elasticity force of the spring 8d. This ability to move in the advancing direction V is advantageous for activating the dosing and activating means, which due to this feature can spring-deflect into itself.

In the following, the components 8a to 8d may be referred to together or in their entirety as the dosing and activating button 8.

It should also be understood that an encircling groove 9 is formed on the outer surface area of the dosing and activating button 8, in the exemplary embodiment on the outer surface area of the outer sleeve part 8a, in a portion surrounding the transfer element 10. Said groove 9 co-operates with a blocking member, such as blocking ring 45 which is formed annularly, that may surround the outer surface area of the dosing and activating button 8, and may be tensed radially inwardly against the outer surface area of the dosing and activating button 8 by means of a spring element 49.

Figure 9:
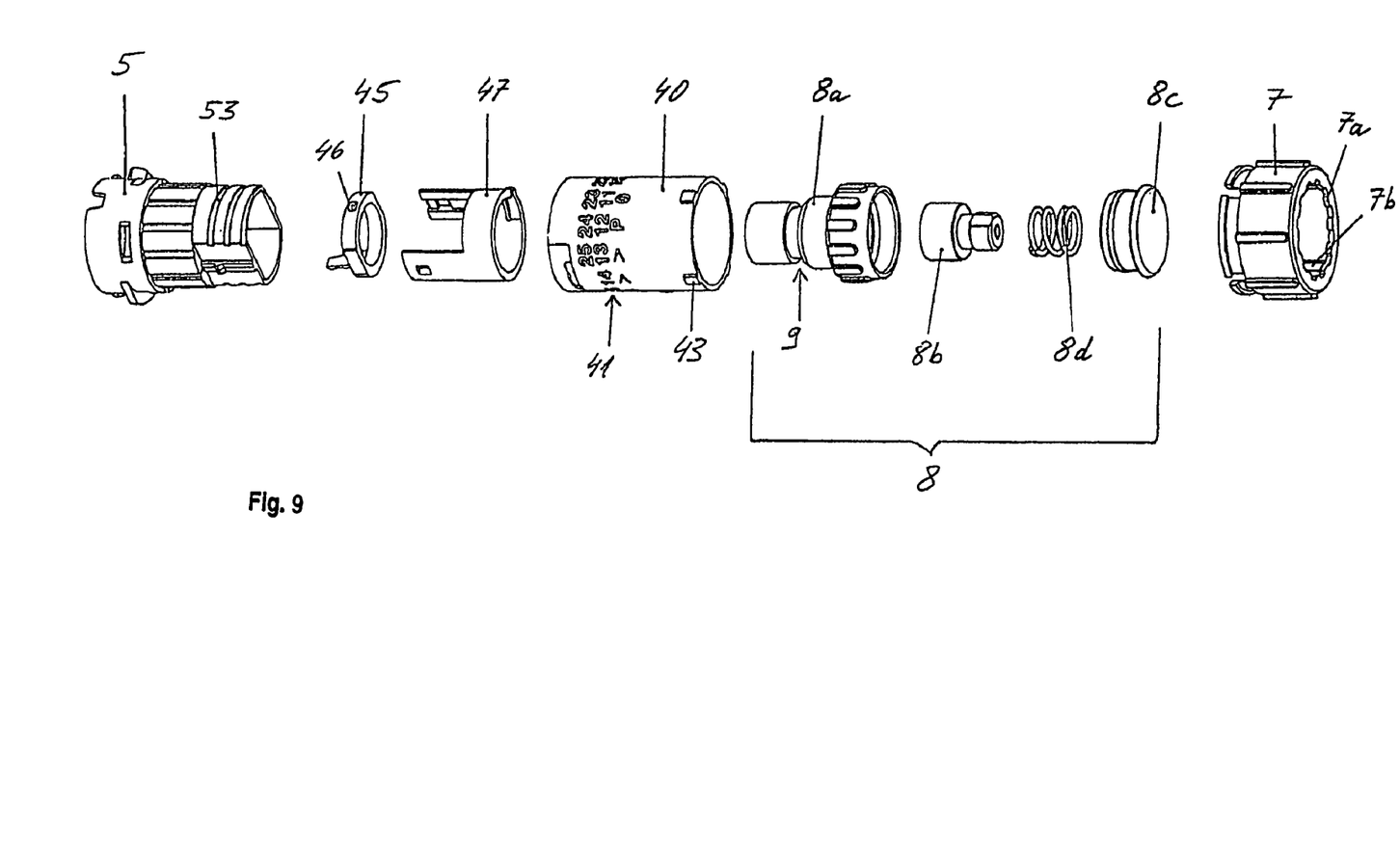
FIG. 9 depicts a dosage indicator sleeve and components co-operating with a dosage indicator sleeve, in a three-dimensional representation.
Figure 10A:
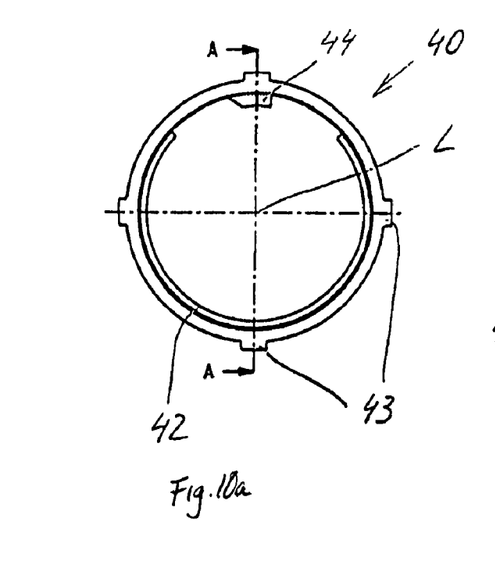
Figure 10B:
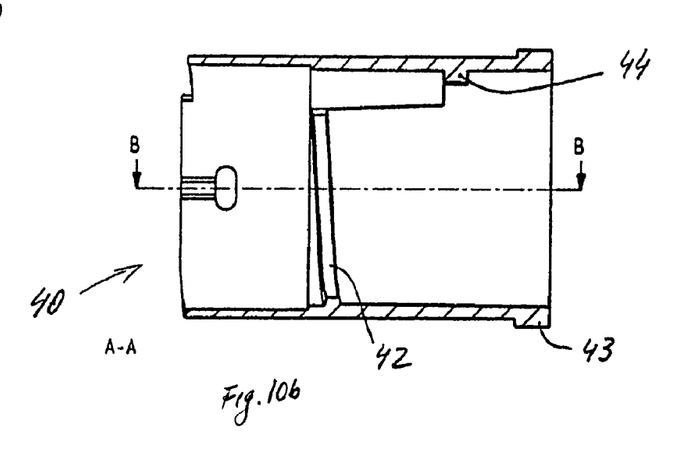
Figure 10C:
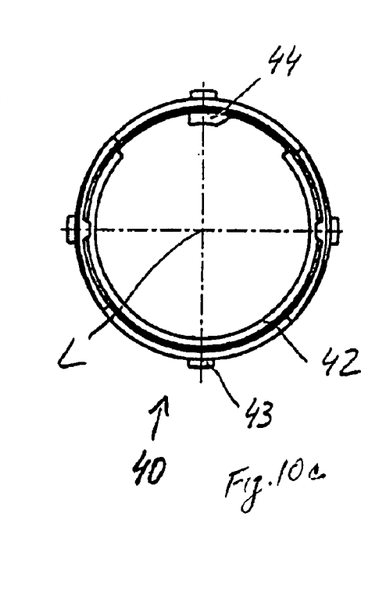
Figure 10D:
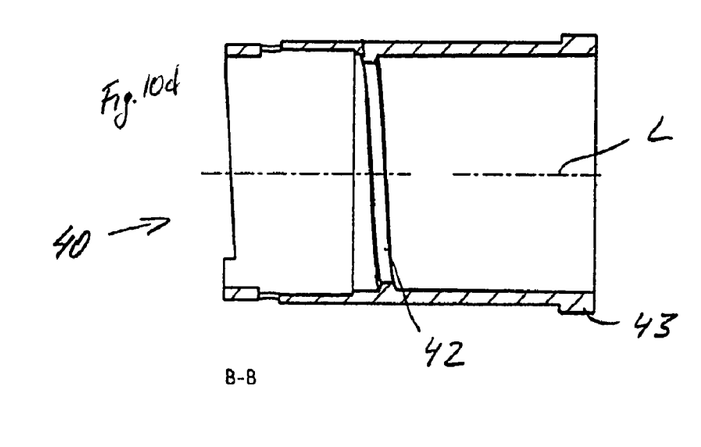

The dosing sleeve 7 is attached to the rear end of the rear casing portion 2 and can be rotated about the longitudinal axis L, relative to the rear casing portion 2. At its rear end, the dosing sleeve 7 forms a collar which protrudes radially inwardly and forms teeth 7a (FIG. 9) uniformly distributed over its inner circumference. On an outer surface area opposite the teeth 7a, the dosing and activating button 8 forms linear, axial guiding grooves at a corresponding pitch, in each of which one of the teeth 7a is axially and linearly guided. In this way, the dosing sleeve 7 and the dosing and activating button 8 are secured against rotating about the longitudinal axis L, but are connected such that they can move axially relative to each other.

A piston rod holder 6 forms an axial linear guide for the piston rod 4. The piston rod holder 6 is connected to the rear casing portion 2 such that it cannot move, in particular the piston rod holder 6 can neither be axially moved relative to the rear casing portion 2 or rotated about the longitudinal axis L. The piston rod holder 6 and the piston rod 4 can only move axially relative to each other. In this way, the piston rod 4 is axially and linearly guided relative to the rear casing portion 2.

Between a rear end of the piston rod holder 6 and a collar, protruding radially inwardly, of a mechanism holder 5, a sliding piece 15 is radially mounted over the first dosing member 11 and another sliding piece 16 is radially mounted over the second dosing member 12, each secured against shifting axially, but radially and linearly guided and in this sense able to move radially. The sliding pieces 15 and 16 have substantially the same form and fulfill substantially the same function, each with respect to the assigned or respective first dosing member 11 and second dosing member 12. The sliding pieces 15 and 16 are arranged symmetrically with respect to the longitudinal axis L. The mechanism holder 5 is connected immovably to the rear casing portion 2, in particular it cannot move axially relative to the rear casing portion 2, to which end the three-quarter rib 56 serves as a stopper, and cannot rotate about the longitudinal axis L. may surround the outer surface area of the dosing and activating button 8, and The gear output members 15 and 16 arranged as sliding pieces form additional gear members or components of the cam gear, and are each in direct engagement with one of the dosing members 11 and 12. Gear output members 15 and 16 each co-operate with a gear input member 20 formed as a sliding sleeve. The gear input member 20 forms another cam member and the two gear output members 15 and 16 each form an engagement member of the cam gear. The gear input member 20 can be axially moved relative to the first dosing member 11 and second dosing member 12, the two gear output members 15 and 16, and relative to the rear casing portion 2. Furthermore, it can be rotated about the longitudinal axis L relative to the rear casing portion 2. A circular cylindrical inner surface area of the mechanism holder 5 forms a rotational sliding bearing and an axial linear guide for the gear input member 20.

Figure 4:
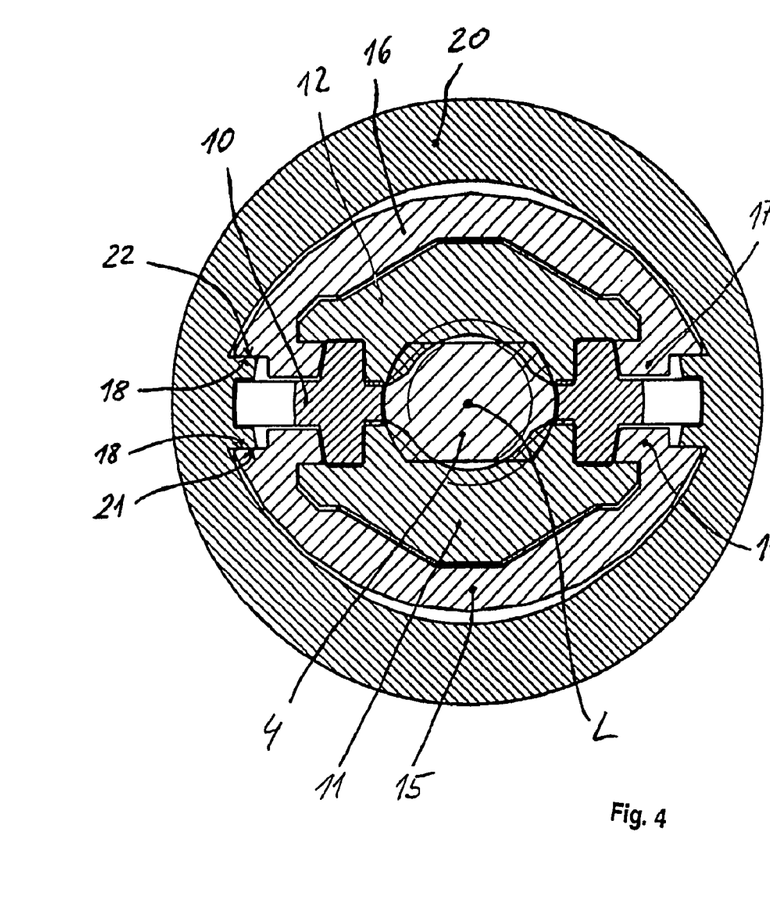
FIG. 4 is a cross-section along line A-A of FIG. 2.
Figure 5:
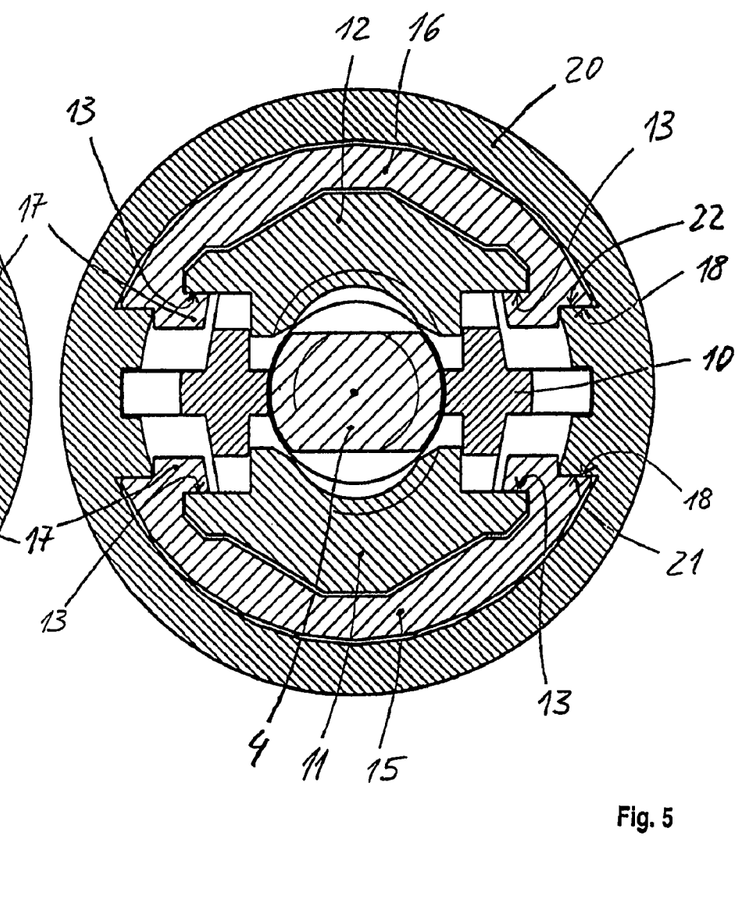
FIG. 5 is a cross-section along line B-B of FIG. 3.
Figure 6:
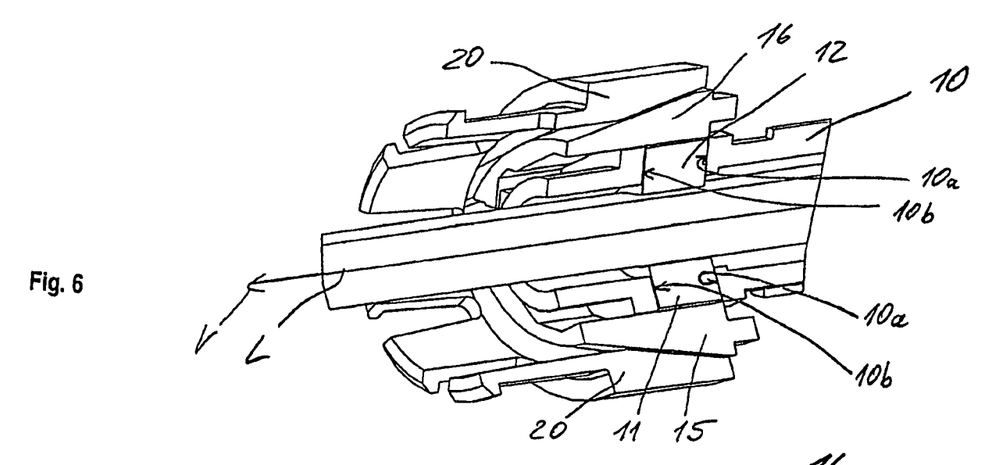
FIG. 6 depicts a piston rod, a dosing member and gear members of a cam gear in a three-dimensional section, wherein the piston rod and the dosing member are in engagement.
Figure 7:
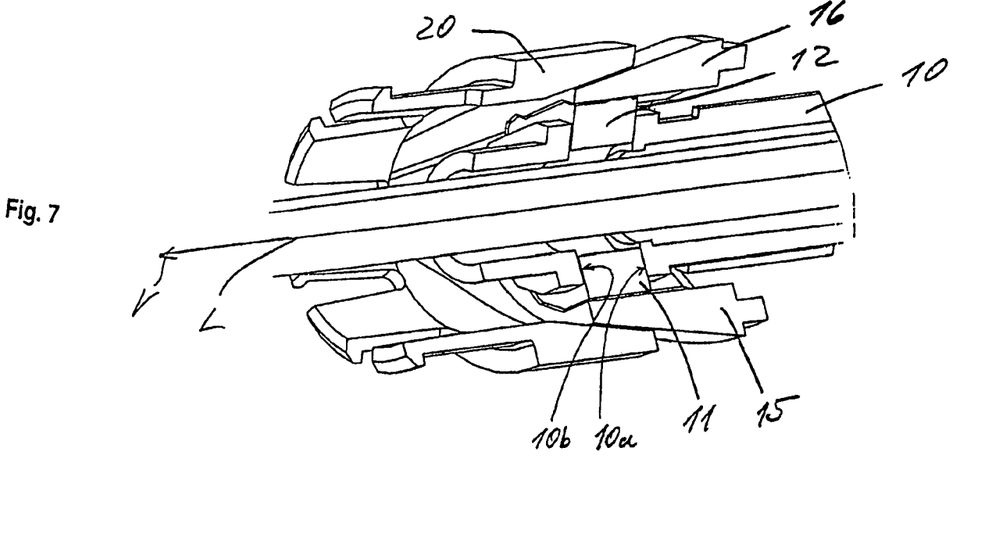
FIG. 7 depicts the piston rod, the dosing member and the gear members in a three-dimensional section, wherein the piston rod and the dosing member are out of engagement.

FIGS. 4 and 5 show the cam gear with the split dosing member (comprising members 11, 12) and the piston rod 4, each in the same cross-section, relative to the dosing member, but in different gear states. The same gear states are shown in FIGS. 6 and 7, each in a three-dimensional section. Regarding the mode of operation of the cam gear, reference may additionally also be made to FIGS. 4 to 7.

The gear output members 15, 16 arranged as sliding pieces are each conical on their outer surface. The gear input member 20, arranged as a sliding sleeve forms a corresponding counter cone on its inner surface facing the conical areas of the gear output members 15, 16. The conical outer areas of the gear output members 15, 16 and the area of the counter cone of the gear input member 20 are parallel to each other, forming a conical gap which is uniformly wide over the entire conical areas.

As can be recognized in FIGS. 4 and 5, the gear input member 20 forms two guiding rails 21 for the gear output member 15 and two guiding rails 22 for the gear output member 16. The gear output members 15, 16 form corresponding engagement rails 18 which are in sliding contact with the guiding rails 21, 22. The guiding rails 21 are formed on the inner surface area of the gear input member 20, diametrically opposed to each other on both sides of the longitudinal axis L. The same applies to the guiding rails 22. The guiding rails 21, 22 extend in the axial direction and each exhibits, in one embodiment, a substantially constant inclination with respect to the longitudinal axis L, i.e., the guiding rails 21, 22 are linear. The guiding rails 21 are generally parallel to each other, and the guiding rails 22 are also generally parallel to each other. The guiding rails 21, 22, formed on the left-hand side and right-hand side of the gear input member 20 in the cross-section in FIGS. 4 and 5, run sagittally towards each other in the advancing direction V—as seen in the longitudinal section in FIG. 1—at an acute angle bisected by a straight line parallel to the longitudinal axis L. When the gear input member 20 moves axially relative to the gear output members 15, 16, the gear output members 15, 16 are thus guided via their engagement rails 18 on the guiding rails 21, 22, such that the gear output members 15, 16 are moved away from each other or towards each other transversely with respect to the longitudinal axis L, in this exemplary embodiment, substantially exactly perpendicularly with respect to the longitudinal axis L.

The first dosing member 11 is accommodated, axially and linearly guided, in the gear output member 15. The second dosing member 12 is correspondingly accommodated, axially and linearly guided, in its gear output member 16. On their mutually facing lower sides, on the left-hand and right-hand side in the cross-section, the gear output members 15, 16 arranged as sliding pieces comprise stays 17 which protrude or extend inwardly toward each other. The gear output member 15 grips behind the first dosing member 11 with its two stays 17 and the output member 16 grips behind the second dosing member 12 with its two stays 17. If the two gear output members 15, 16 are moved away from each other, transversely with respect to the longitudinal axis L, then the stays 17 gripping behind the dosing members 11, 12 move the two dosing members 11, 12 away from each other, transversely with respect to the longitudinal axis L, in the same way, and thus move them out of engagement with the piston rod 4. When the gear output members 15, 16 move transversely towards each other, the gear output members 15, 16 again also press the dosing members 11, 12 towards each other via their surface areas, and thus back into engagement with the piston rod 4. As already mentioned, the dosing members 11, 12 are axially guided in their respective gear output members 15, 16 such that they can shift linearly. The stays 17 form guiding rails for the linear guide, and the dosing members 11, 12 form engagement rails 13 guided on them, which the stays 17 grip behind.

The threaded engagement between the piston rod 4 and the split dosing member (comprising members 11, 12) which exists in the state in FIG. 1 is released by the casing portions 1, 2 moving axially relative to each other. This relative movement occurs when the casing portions 1, 2 are screwed apart. When the casing portions 1, 2 are screwed apart, the casing formed jointly by the casing portions 1, 2 is initially lengthened, which corresponds to the casing portions 1, 2 moving axially relative to each other. The relative movement between the casing portions 1, 2, required for example for exchanging the reservoir R, is thus used to release the engagement between the piston rod 4 and the split dosing member, and the block against the piston rod 4 and the dosing and activating means axial shifting obtained by this engagement.

In order to be able to use the casing portions 1, 2 moving axially relative to each other to release the engagement, the gear input member 20 arranged as a sliding sleeve is connected to the front casing portion 1 in such a way that it is slaved in its axial movement relative to the rear casing portion, while the gear output members 15, 16, e.g., arranged as sliding pieces, retain their axial position relative to the rear casing portion 2. Mounting the gear output members 15, 16 between the mechanism holder 5 and the piston rod holder 6 ensures, as mentioned, that the gear output members 15, 16 are secured against shifting axially. The coupling of the gear input member 20 on the front casing portion 1 forms a reservoir holding spring 37 which is axially pressure-tensed between the piston rod holder 6 and a reservoir holder 30 when the two casing portions 1 and 2 are completely screwed together. To this end, the reservoir holding spring 37 is tensed between the piston rod holder 6 and the reservoir holder 30. The reservoir holding spring 37 presses the reservoir holder 30 against the rear edge of the container which forms the reservoir R. The reservoir holding spring 37 presses the container against a stopper area formed in the front casing portion 1. Arranging such a reservoir holding spring 37 is common in order to equalise length tolerances of the container, the casing portions 1, 2 and the components on which the container is supported in the longitudinal direction.

A slaving means 25 is fastened, secured against shifting and secured against rotating, to the reservoir holder 30. The slaving means 25 forms a transfer member between the reservoir holder 30 and the gear input member 20, when the reservoir holder 30 follows an axial movement of the front casing portion 1 due to the spring force of the reservoir holding spring 37. The gear input member 20 and the slaving means 25 grip behind each other such that the gear input member 20 is slaved by the slaving means 25 during the axial movement. In the exemplary embodiment, a tolerance equalisation spring 38 is axially tensed between the gear input member 20 and the slaving means 25. In principle, however, the gear input member 20 and the slaving means 25 could also be rigidly connected to each other with respect to the axial direction. In any event, a rotational movement about the longitudinal axis L is possible between the gear input member 20 and the slaving means 25. In this respect, the rotational joint between the dosing and activating means and the rear casing portion 2 is formed between the gear input member 20 and the slaving means 25.

How the gear components 20, 25 and 30 are assembled and arranged relative to the piston rod holder 6 in one embodiment can be understood with reference to FIG. 8. The mutually facing collars 31 and 61 of the reservoir holder 30 and piston rod holder 6 in particular can for instance be recognised, between which the reservoir holding spring 37 is tensed. The reservoir holder 30 comprises a generally circular and cylindrical front sleeve part including a collar 31. Multiple shoes 32 project backwards from the sleeve part. A locking cam 34 which protrudes radially outwardly is formed at the rear end of each of the shoes 32. Furthermore, each of the shoes 32 comprises lateral guides 33. The reservoir holder 30 together with its shoes 32 can be inserted between a radially outer and middle sleeve part of the piston rod holder 6. To this end, a sleeve base of the piston rod holder 6 comprises cavities corresponding to the shoes 32. The piston rod holder 6 and the reservoir holder 30 are connected to each other, secured against rotating, via the shoes 32 and the cavities. From the rear side, the slaving means 25 is pushed onto the reservoir holder 30 via the middle sleeve part of the piston rod holder 6. Tongues 27 project from a rear sleeve part of the slaving means 25, corresponding in number and arrangement to the shoes 32. Each one of the tongues 27 is pushed onto one of the shoes 32 and locked by means of the locking cams 34, wherein the locking cams 34 lock into cavities 28 formed correspondingly on the tongues 27. The connection between the slaving means 25 and the reservoir holder 30 can be regarded as substantially completely rigid.

The gear input member 20 arranged as a sliding sleeve comprises a rear sleeve part and a plurality of elastically bending tongues 23, which project from the sleeve part and protrude towards the slaving means 25 in the advancing direction V. Slaving cams 24 are formed at the front ends of the tongues 23 and project radially outward from the tongues 23. When the slaving means 25 moves axially, the gear input member 20 is slaved by an engagement which exists when the slaving cams 24 are connected to a slaving collar 26 which protrudes radially inwardly at the rear end of the slaving means 25 and which the slaving cams 24 grip behind when connected. The engagement simultaneously enables relative rotational movements about the longitudinal axis L.

Furthermore, it can also be recognized in FIG. 8 how the mechanism holder 5 and the piston rod holder 6 are connected, secured against shifting and secured against rotating. Elastically bending tongues 63 comprising locking cams 64 protruding radially outwardly, project backwards from the sleeve part of the piston rod holder 6. Via the locking cams 64, the piston rod holder 6 locks in corresponding cavities 52 of the mechanism holder 5. Furthermore, a block against rotating between the mechanism holder 5 and the piston rod holder 6 is obtained by engaging a guiding protrusion 62, which axially projects from the piston rod holder 6, with a guiding cavity 51 of the mechanism holder 5. The mechanism holder 5 and the piston rod holder 6 are connected to each other, secured against shifting and secured against rotating, via the locking connection of the locking cam 64 and the guide of the guiding protrusion 62. The mechanism holder 5 is connected to the rear casing portion 2, secured against shifting and secured against rotating, such that the same also applies to the piston rod holder 6.

A restoring spring 36 is axially tensed between the piston rod holder 6 and the transfer element 10 of the dosing and activating means. The restoring spring 36 serves to restore the dosing and activating means, the split dosing member and the piston rod 4, after the product has been delivered.

The device further comprises a dosage indicator sleeve 40, which is provided on its outer surface area with a dosage scale 41. The dosage indicator sleeve 40 is shown in a three-dimensional view from the side in each of FIGS. 8 and 9, and in two longitudinal sections, a front view and a rear view in FIG. 10. It is in threaded engagement with the mechanism holder 5. The threaded engagement exists between an outer thread 53 in a rear portion of the mechanism holder 5 and an inner thread 42 of the dosage indicator sleeve 40. The threaded axis of the two threads 42 and 53 coincides with the longitudinal axis L. The dosage scale 41 is formed by dosage values arranged, encircling in a spiral, on the outer surface area of the dosage indicator sleeve 40. In the exemplary embodiment, numbers corresponding to the dosage units which can be selected form the dosage values. The dosage indicator sleeve 40 is connected to the dosing sleeve 7 such that it can be axially and linearly shifted but is secured against rotating with respect to the longitudinal axis L. For this purpose, the rear end of the dosage indicator sleeve 40 comprises a plurality of radially projecting guiding cams 43 which protrude into and are axially and linearly guided in corresponding guiding grooves 7b (FIG. 9) on the inner surface area of the dosing sleeve 7. Due to this engagement, the dosage indicator sleeve 40 is also rotated about the longitudinal axis L when the dosing sleeve 7 is rotated. Due to the threaded engagement with the mechanism holder 5, the dosage indicator sleeve 40 is thus screwed backwards, counter to the advancing direction V, relative to the mechanism holder 5 and therefore also relative to the rear casing portion 2, when the dosage is selected by rotating the dosing sleeve 7.

The portion of the dosage indicator sleeve 40 which forms the inner thread 42 and the dosage scale 41 protrudes into an annular gap which remains between the rear casing portion 2 and the mechanism holder 5. In the radially outer portion opposing the dosage scale 41, the rear casing portion 2 comprises a window 3 through which the dosage scale 41 can be read. The pitch of the inner thread 42 corresponds to the pitch of the spiral dosage scale 41.

The blocking ring 45 may be arranged radially inwardly from a longitudinal portion of the dosage indicator sleeve 40, which protrudes backwards beyond the mechanism holder 5. The blocking ring 45 is mounted, secured against rotating and secured against shifting axially, in a sleeve part of a blocking ring holder 47. The blocking ring holder 47 is fastened, secured against rotating and shifting, to the mechanism holder 5, via a guiding area 54 of the mechanism holder 5 and a locking connection formed between a locking cam 55 of the mechanism holder 5 and a cavity 48 of the blocking ring holder 47 (FIG. 8).

The blocking ring 45 forms a counter reset cam 46 which protrudes radially outwardly from the outer surface area of the blocking ring 45 towards the dosage indicator sleeve 40. A reset cam 44 projects radially inwardly from the facing inner surface area of the dosage indicator sleeve 40 (FIG. 10). The reset cam 44 is formed in a rotational angular position with respect to the dosage scale 41, such that it is in radial alignment with the counter reset cam 46 and presses radially against the cam 46 precisely when the dosage indicator sleeve 40 assumes a zero-dosage position relative to the rear casing portion 2, in which the dosage value corresponding to the zero-dosage is indicated in the window 3. If the dosage indicator sleeve 40 assumes a position with respect to the mechanism holder 5 and the rear casing portion 2 which does not correspond to the zero-dosage, then the counter reset cam 46 is free from the reset cam 44, i.e., a radially slight distance remains between the counter reset cam 46 and the facing inner surface area of the dosage indicator sleeve 40.

The blocking ring 45 can be moved linearly relative to the blocking ring holder 47, radially with respect to the longitudinal axis L. Diametrically opposite the counter reset cam 46 with respect to the longitudinal axis L, the spring element 49 is arranged between the blocking ring 45 and the blocking ring holder 47 and presses the blocking ring 45 against the outer surface area of the dosing and activating button 8. The spring element 49 acts as a pressure spring.

The functionality and method of operation of the device in accordance with the present invention is described below with reference to FIGS. 1 to 3, in each of which the device is shown in a different state. Reference should additionally be made to the other figures.

In FIG. 1, the device assumes an initial state in which the reservoir R is completely filled with the product and from which the dosage can be selected. The dosage or dose indicator sleeve 40 assumes its position corresponding to the zero-dosage, i.e., the dosage value corresponding to the zero-dosage can be read through the window 3. The dosing and activating means (comprising the dosing sleeve 7, the dosing and activating button 8 and the transfer element 10), together with the piston rod 4, assumes its rearmost position, in which the dosage is selected. In this dosage selection position, a slight axial distance $H_1$ remains between the piston rod 4 and the piston K. An equally large, slight axial distance $H_2$ remains between two stopper areas which face each other axially, one of which is formed by the piston rod holder 6 and the other of which is formed by the transfer element 10 and which define a front end position for the transfer element 10 and the piston rod 4. The slight axial distance $H_2$ between this pair of stopper areas is the maximum stroke of the piston rod 4. Selecting the dosage reduces the slight axial distance $H_1$ between the piston K and the piston rod 4. If, within the context of the delivery movement, the piston rod 4 is then moved in the advancing direction V by the always equally long stroke $H_2$ as far as its front end position, then the reduction in the slight distance $H_1$ between the piston rod 4 and the piston K while selecting the dosage corresponds to the product dosage delivered.

The split dosing member (comprising members 11, 12) is coupled to the dosage indicator sleeve 40 via the dosing and activating means, such that the axial distance $H_1$ between the piston K and the piston rod 4 is at a maximum, i.e., $H_1=H_2$, when the dosage indicator sleeve 40 assumes its zero-dosage position.

To select the dosage, the dosing sleeve 7 is rotated about the longitudinal axis L relative to the rear casing portion 2, wherein the dosing and activating button 8 is also rotated due to its engagement, secured against rotating, with the dosing sleeve 7. Due to these connections, secured against rotating, the transfer element 10 and therefore also the split dosing member are also necessarily rotated together. Since the piston rod 4 is axially and linearly guided by the piston rod holder 6, the rotational movement of the split dosing member causes a dosing movement of the piston rod 4 directed in the advancing direction, via the threaded engagement. This shortens the slight distance $H_1$ between the piston rod 4 and the piston K by a length corresponding to the selected product dosage; it does not alter the slight distance $H_2$.

Due to its engagement, secured against rotating, the dosage indicator sleeve 40 is slaved or driven or moved correspondingly by the dosing sleeve 7 during the rotational dosing movement and is rotated about the longitudinal axis L relative to the mechanism holder 5. Due to the threaded engagement between the mechanism holder 5 and the dosage indicator sleeve 40, an axial movement counter to the advancing direction V is superimposed on the rotational movement of the dosage indicator sleeve 40. As an aside, it should be understood that, in one embodiment, the pitch of the engaged threads 42 and 53 of the dosage indicator sleeve 40 and mechanism holder 5 is greater than the pitch of the engaged threads of the piston rod 4 and split dosing member. Correspondingly, the axial path which the dosage indicator sleeve 40 travels per revolution is larger than the axial path by which the piston rod 4 is moved per revolution of the split dosing member. This benefits the legibility of the dosage scale 41. As soon as the dosage indicator sleeve 40 has been moved, relative to the mechanism holder 5, out of its zero-dosage position by at least one dosage unit, the blocking ring 45 is free from the reset cam 44. The dosage value which can be read on the dosage scale 41 through the window 3 corresponds to the axial length by which the distance $H_1$ is shortened by the dosing movement.

In order to deliver the selected product dosage through the outlet A of the reservoir R, the dosing and activating button 8 is pressed in the advancing direction V, into the rear casing portion 2, i.e., it is activated. The advancing direction V is therefore also simultaneously the activating direction of the dosing and activating button 8. Activating the dosing and activating button 8 also moves the components which are connected, secured against shifting axially, to the dosing and activating button 8, namely the transfer element 10, the split dosing member and, due to the threaded engagement, also the piston rod 4, in the advancing direction V by the stroke length $H_2$. During this stroke movement, the piston K is advanced in the advancing direction V by a path length which corresponds to the length by which the slight distance $H_1$ between the piston rod 4 and the piston K is shortened as compared to the stroke $H_2$ by selecting the dosage.

FIG. 2 shows the device in an end state in which, after repeated administering, the maximum product amount which can be delivered from the reservoir R with the aid of the device has been delivered, i.e., the reservoir R has been emptied. The dosing and activating button 8 has been pressed into the rear casing portion 2 by the stroke length $H_2$. In this axial position of the dosing and activating button 8, its groove 9 is in radial alignment below the blocking ring 45. The groove 9 is slightly wider in the radial direction than the blocking ring 45, in order to still be able to accommodate the blocking ring 45 when the dosing and activating button 8 is spring-deflected. For the pressure from the user, required for activating the dosing and activating button 8, spring deflects the dosing and activating button 8 a little way into itself, in the front end position of the transfer element 10 and the piston rod 4, which is regarded as touch pleasing. Since the blocking ring 45 is tensed against the outer surface area of the dosing and activating button 8 by the spring element 49, the blocking ring 45 is inserted radially into the groove 9 which is then accessible for it. The larger width of the groove 9 as compared to the blocking ring 45, in combination with the axial spring-deflection of the dosing and activating button 8, increases the reliability that the blocking ring 45 will indeed be inserted into the groove 9 and the dosing and activating means blocked. The blocking ring 45 forms an axial stopper for the spring-deflection movement of the dosing and activating button 8. Diametrically opposite the spring element 49, inserting the blocking ring 45 moves its counter reset cam 46 radially toward the inner surface area of the dosage indicator sleeve 40. Since the blocking ring 45 is connected to the mechanism holder 5 such that it cannot move axially in the blocking ring holder 47, the dosing and activating button 8 and therefore the piston rod 4 together cannot be moved back again counter to the advancing direction V, i.e., the blocking ring 45 and the dosing and activating button 8 are in a blocking engagement. Thus, in the foremost position of the dosing and activating means, the blocking-engaged blocking ring 45 seated in the groove 9 forms an axial block for the dosing and activating means, the split dosing member and the piston rod 4. In this end state, the restoring spring 36 is axially pressure-tensed. The restoring spring 36 is prevented from being relieved by the axial block formed by the blocking ring 45. This axial block ensures that the product can only be selected anew from a defined position of the dosage indicator sleeve 40. This defined position is preferably—as in this exemplary embodiment—the zero-dosage position, i.e., the position in which the zero-dosage can be read on the dosage scale 41 through the window 3.

In order to exchange the emptied reservoir R for a new reservoir R, the two casing portions 1 and 2 are screwed apart. Due to the screwing procedure, the casing portions 1 and 2 are moved axially relative to each other. During the movement of casing portions 1 and 2 which lengthens the casing, the tensed reservoir holding spring 37 presses the reservoir holder 30 relative to the piston rod holder 6 in the advancing direction V until it abuts a stopper formed by the rear casing portion 2. Before the screwing movement is begun, a sufficiently large, slight distance remains axially between a front end of the reservoir holder 30 and the stopper formed by the rear casing portion 2, to enable the reservoir holder 30 to move axially relative to the piston rod holder 6.

As the reservoir holder 30 moves axially relative to the piston rod holder 6, it slaves the slaving means 25 and the gear input member 20. Due to the axial movement of the gear input member 20, the two gear output members 15, 16 move generally radially outwardly on the oblique guiding rails 21, 22 of the gear input member 20. As they move radially outwardly in this way, the gear output members 15, 16 are linearly guided by the mechanism holder 5 and the piston rod holder 6. Since the stays 17 of the gear output member 15 grip behind the first dosing member 11 and the stays 17 of the gear output member 16 grip behind the second dosing member 12, the first dosing member 11 and the second dosing member 12 are moved radially apart in the same way, and are thus moved out of their threaded engagement with the piston rod 4. The axial movement which the rear casing portion 2 performs relative to the front casing portion 1 in order to release the engagement between the piston rod 4 and the dosing members 11, 12 may be referred to as a disengaging movement. The disengaging movement moves each of the dosing members 11, 12 to a position retracted from the piston rod 4. In the opposite, engaging movement, in which the rear casing portion 2 performs an axial movement in the reverse direction relative to the front casing portion 1, the dosing members 11, 12 are moved back into engagement with the piston rod 4 by the cam gear formed by gear input member 20 and the gear output members 15, 16. Starting with the casing portions 1 and 2 completely screwed together, the disengaging movement and the engaging movement occur in a first portion of the screwing movement. This first portion of the screwing movement is complete when the reservoir holding spring 37 has pressed the reservoir holder 30 against the stopper formed by the rear casing portion 2.

FIG. 3 shows the device in a state in which the threaded engagement between the split dosing member and the piston rod 4 has been released and the piston rod 4 can thus be freely shifted axially in the piston rod holder 6. The rear casing portion 2 has just completed its disengaging movement. In the state shown, the piston rod 4 has already been reset or returned to its rearmost position. The piston rod 4 can thus slide back, guided by the piston rod holder 6, to the end position shown, for example by gently tilting the entire device. At the rear end of the dosing button 8, a rubber stopper S projects inwards in the advancing direction V and gently damps or stops the sliding movement of the piston rod 4.

As the casing portions 1, 2 are screwed further apart, the positions assumed by the dosing members 11, 12, the gear output members 15, 16, the gear input member 20 and the reservoir holder 30 relative to the rear casing portion 2 are no longer altered. This is ensured by the reservoir holder 30 abutting the rear casing portion 2. The two casing portions 1, 2 can be screwed completely apart and the spent reservoir R exchanged for a new one. Once a new reservoir R has been inserted into the front casing portion 1, the two casing portions 1, 2 are screwed back together. In the final portion of the screwing movement, the rear casing portion 2 performs its engaging movement relative to the front casing portion 1, in which the reservoir holder 30 comes into contact with the reservoir R or a reservoir holder and is pressed by the latter axially towards the piston rod holder 6, against the spring force of the reservoir holding spring 37. As it axially moves, the reservoir holder 30 also presses the sliding gear input member 20, via the slaving means 25, backwards counter to the advancing direction V. This moves the gear output members 15, 16 arranged as sliding pieces radially inwardly via their guiding engagement with the sliding sleeve 20, until the synchronous engagement between the dosing members 11, 12 and the piston rod 4 is re-established.

While, in the above, resetting the piston rod 4 is only described for a completely spent reservoir R, it should be noted that the piston rod 4 can also be reset in accordance with the invention from any other axial position of the piston rod 4 in which the piston rod 4 has been moved out of its rearmost position shown in FIG. 1 by a rotational dosing movement by the split dosing member.

When the dosing and activating button 8 is pressed into in the rear casing portion 2 to its foremost position, as is shown in FIGS. 2 and 3, there is no longer a block against rotating between the dosing sleeve 7 and the dosing and activating button 8, i.e., the dosing sleeve 7 can be freely rotated about the longitudinal axis L relative to the dosing and activating button 8 and rear casing portion 2. However, the block against rotating between the dosing sleeve 7 and the dosage indicator sleeve 40 still exists. In order to return the dosing and activating button 8, and therefore the dosing and activating means and split dosing member together, to the dosage selection position, the dosing sleeve 7 is rotated about the longitudinal axis L in a rotational direction which guides the dosage indicator sleeve 40 back to the zero-dosage position. During this rotational movement, the dosage indicator sleeve 40 is rotated relative to the mechanism holder 5. As a result of the threaded engagement with the mechanism holder 5, the dosage indicator sleeve 40 completes a translational and rotational movement relative to the mechanism holder 5 and rear casing portion 2, towards its zero-dosage position. In a final movement portion before reaching the zero-dosage position, the length of which corresponds to a single settable dosage unit, the reset cam 44 of the dosage indicator sleeve 40 radially overlaps with the counter reset cam 46 of the blocking ring 45. The reset cam 44 is tapered in the circumferential direction on the side which presses against the counter reset cam 46 while the dosage indicator sleeve 40 is rotated back. Tapering enables the two cams 44, 46 to gradually and gently slide over each other. The reset cam 44, which gradually lengthens radially inwardly in its tapered region, moves the blocking ring 45 radially out of the groove 9, against the restoring force of the spring element 49. The axial block is thus released, and the restoring spring 36 presses the dosing and activating means, together with the piston rod 4, back to the initial position shown in FIG. 1.

In one embodiment, the sequence of selecting the dosage, delivering the selected dosage by activating the dosing and activating means, axially blocking with the blocking ring 45 via the cam 46, rotating the dosage indicator sleeve 40 back to the zero-dosage position and thus releasing the axial block and springing the dosing and activating means back to the initial position, can be repeated until the reservoir R has been emptied. The cam 46 and reset cam 44 co-operation couples the movement of the dosing and activating means back to the initial position, from which a dosage can be selected anew, to the zero-dosage position of the dosage indicator sleeve 40. This coupling is advantageously configured such that on the one hand, the movement of the dosing and activating means is only possible when the dosage indicator sleeve 40 assumes its zero-dosage position, but on the other hand, no other hand operations are required in order to trigger the resetting movement of the dosing and activating means.

In some embodiments, the delivery device in accordance with the present invention is provided for or maybe used with an inhaler such as those known to those skilled in the art, using which insulin is administered via the airways. The device serves to dose and deliver the product into an atomising chamber. The product thus provided in doses in the atomising chamber is atomised by an atomising means and administered through a chamber outlet via the airways, preferably orally. The front end of the front casing portion 1 may be provided with a suitable connector G formed as a thread, in order to be able to connect the device to the atomising chamber by threaded engagement.

In some embodiments, the device in accordance with the present invention may also be used directly as an injection apparatus, by screwing a needle holder comprising an integrated injection needle of preferably 30 G or thinner, for example 31 G, onto the front end of the front casing portion 1. In some embodiments, the device could also be provided for or used with a pressure injector such as those known to those skilled in art and, in this case, could be connected to a discharge means of the pressure injector. The device would supply the selected product dosage to the discharge means and the discharge means would discharge said product dosage at high pressure through an injection nozzle.

In the foregoing description, embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A product delivery device with rapid piston rod resetting, said device comprising: a) a casing comprising a first casing portion for a reservoir which is filled with product and from which the product can be delivered by means of a piston; b) a piston rod which can be moved in an advancing direction in order to move the piston towards an outlet of the reservoir in order to deliver the product; c) a dosing and activating means which performs a dosing movement relative to the casing and, together with the piston rod performs a delivery movement in the advancing direction, relative to the casing; d) a dosing member coupled to the dosing and activating means such that it is slaved in the delivery movement and during dosing performs a dosing movement, and which is in engagement with the piston rod which permits the dosing movement of the dosing member relative to the piston rod, and which slaves the piston rod during the delivery movement; e) wherein the dosing member can be moved transversely with respect to the piston rod, in order to release the engagement with the piston rod for resetting the piston rod counter to the advancing direction; f) a resetting and activating element movably coupled to the casing in order to perform a disengaging movement and an engaging movement; g) and a cam gear which couples the resetting and activating element to the dosing member, such that the dosing member is moved out of engagement with the piston rod by the disengaging movement and into engagement with the piston rod by the engaging movement, the cam gear comprising a gear input member coupled to the resetting and activating element and a gear output member coupled to the dosing member, wherein the gear input member and the gear output member are in an engagement which converts a movement caused by the engaging movement and the disengaging movement of the resetting and activating element, which the gear input member performs relative to the gear output member, into a movement of the gear output member transversely with respect to the piston rod; h) wherein the cam gear forms a transverse guiding rail which points transversely with respect to the advancing direction and on which the dosing member is guided when moving into and out of engagement.

2. The product delivery device as set forth in the claim 1, wherein one of the gear output member and the gear input member forms an additional guiding rail and, in engagement, the other of the gear output member and the gear input member forms an engagement member guided on the additional guiding rail.

3. The product delivery device as set forth in claim 2, wherein the additional guiding rail exhibits an inclination with respect to the piston rod in the longitudinal direction of the piston rod.

4. The product delivery device as set forth in claim 2, wherein the additional guiding rail runs such that a relative movement between the gear input member and the gear output member along a longitudinal axis of the piston rod causes the gear input member to move the gear output member into or out of a compressed engagement which causes the relative movement of the dosing member transversely with respect to the piston rod, by means of the guiding engagement.

5. The product delivery device as set forth in claim 1, wherein the gear input member and the gear output member are conical on mutually facing sides.

6. The product delivery device as set forth in claim 1, wherein the gear output member slaves the dosing member when the gear output member moves transversely with respect to the piston rod.

7. The product delivery device as set forth in claim 6, wherein the gear output member grips behind the dosing member in order to slave the dosing member when the gear output member moves transversely with respect to the piston rod.

8. The product delivery device as set forth in claim 1, wherein the dosing member can be moved in and counter to the advancing direction, relative to the gear output member.

9. The product delivery device as set forth in claim 1, wherein the gear input member is connected to a reservoir holder which is pressed in the advancing direction against a container forming the reservoir, wherein said connection slaves the gear input member when the reservoir holder is moved relative to the dosing member along a longitudinal axis of the piston rod, but permits the gear input member to rotate about the longitudinal axis of the piston rod.

10. The product delivery device as set forth in claim 1, wherein the dosing member, the gear output member and the gear input member are connected to each other, secured against rotating about the longitudinal axis of the piston rod.

11. The product delivery device as set forth in claim 1, wherein a spring element is provided which is tensed by the engaging movement of the resetting and activating element and, during the disengaging movement, moves the gear input member relative to the gear output member, due to its tension force.

12. The product delivery device as set forth in claim 11, wherein a container accommodated by the first casing portion forms the reservoir and in that the spring element presses the container in the advancing direction against a stopper formed by the first casing portion.

13. A product delivery device with rapid piston rod resetting, said device comprising: a) a casing comprising a first casing portion for a reservoir which is filled with product and from which the product can be delivered by means of a piston; b) a piston rod which can be moved in an advancing direction in order to move the piston towards an outlet of the reservoir in order to deliver the product; c) a dosing and activating means which performs a dosing movement relative to the casing and, together with the piston rod performs a delivery movement in the advancing direction, relative to the casing; d) a dosing member coupled to the dosing and activating means such that it is slaved in the delivery movement and during dosing performs a dosing movement, and which is in engagement with the piston rod which permits the dosing movement of the dosing member relative to the piston rod, and which slaves the piston rod during the delivery movement, wherein the dosing member and another dosing member form an axially split threaded nut which is in threaded engagement with the piston rod which is formed as a threaded rod, and in that the dosing members are arranged symmetrically on mutually opposing longitudinal sides of the piston rod; e) wherein the dosing member can be moved transversely with respect to the piston rod, in order to release the engagement with the piston rod for resetting the piston rod counter to the advancing direction; f) a resetting and activating element movably coupled to the casing in order to perform a disengaging movement and an engaging movement; g) and a cam gear which couples the resetting and activating element to the dosing member, such that the dosing member is moved out of engagement with the piston rod by the disengaging movement and into engagement with the piston rod by the engaging movement; h) wherein the cam gear forms a transverse guiding rail which points transversely with respect to the advancing direction and on which the dosing member is guided when moving into and out of engagement.

* * * * *

UNITED STATES PATENT AND TRADEMARK OFFICE
CERTIFICATE OF CORRECTION

| | | |
|---|---|---|
| PATENT NO. | : 7,445,613 B2 | Page 1 of 1 |
| APPLICATION NO. | : 11/023285 | |
| DATED | : November 4, 2008 | |
| INVENTOR(S) | : Edgar Hommann | |

It is certified that error appears in the above-identified patent and that said Letters Patent is hereby corrected as shown below:

On the Title Page

| | | Should Read |
|---|---|---|
| Item (30) | Foreign Application Priority Data | -- June 28, 2002 (DE) ............. 102 29 138 -- |

| Column | Line | | Should Read |
|---|---|---|---|
| 8 | 13-14 | "about the longitudinal axis L. may surround the outer surface area of the dosing and activating button 8, and" | -- about the longitudinal axis L. -- |
| 9 | 17 | "17 and the output member" | -- 17 and the gear output member -- |

Signed and Sealed this

Nineteenth Day of May, 2009

JOHN DOLL
*Acting Director of the United States Patent and Trademark Office*